United States Patent [19]

Johnson

[11] Patent Number: 5,098,298

[45] Date of Patent: Mar. 24, 1992

[54] APPLIANCE AND METHOD OF USE FOR FILLING AN ENDODONTICALLY PREPARED ROOT CANAL

[76] Inventor: William B. Johnson, 5010 E. 68th St., Ste. 104, Tulsa, Okla. 74136

[21] Appl. No.: 687,305

[22] Filed: Apr. 18, 1991

[51] Int. Cl.$^5$ .............................................. A61C 5/02
[52] U.S. Cl. ...................................... 433/224; 433/81
[58] Field of Search .................................. 433/81, 224

[56] References Cited

U.S. PATENT DOCUMENTS

| | | | |
|---|---|---|---|
| 4,457,710 | 7/1984 | McSpadden | 433/81 |
| 4,758,156 | 7/1988 | Johnson | 433/81 |
| 4,894,011 | 1/1990 | Johnson | 433/81 |

Primary Examiner—John J. Wilson
Attorney, Agent, or Firm—Head and Johnson

[57] ABSTRACT

An appliance for use in filling an endodontically prepared root canal being in the form of an elongated shaft having a distal end portion of diameter dimensioned to be received in a root canal and with a spiral thread thereon and having, at the opposite end, a shank portion, filler material formed on the shaft distal end portion, the shaft shank portion being receivable in the chuck of a dental tool having means to rotate the shaft, the shaft distal end portion having the filler material thereon being insertable in a root canal and adapted to be rotated by a dental tool to auger the filler material off of the shaft distal end portion and into the root canal, the shaft being removed from the root canal as the filler material is augured into the canal.

The method of utilizing an apparatus for filling an endodontically prepared root canal includes the steps of forming onto an elongated shaft having a distal end portion of diameter dimensioned to be received in an endodontically prepared root canal and the shaft distal end portion having a spiral thread thereon and having a body of filler material thereon, the shaft having a shank portion, inserting the shank portion into the rotatable chuck of a dental tool, inserting the shaft distal end portion having the filler material thereon into a root canal, and activating the dental tool to rotate the shaft to auger the filler material into the root canal, the shaft being removed from the root canal as the filler material is augered therein.

7 Claims, 2 Drawing Sheets

APPLIANCE AND METHOD OF USE FOR FILLING AN ENDODONTICALLY PREPARED ROOT CANAL

BACKGROUND OF THE INVENTION

The conventional techniques for forming endodontic therapy on teeth are time consuming and often do not accurately ensure that the entire canal system is filled with filler material. The typical means employed by endodonists or dentists performing root canal procedures is to first, thoroughly clean the root canal and remove as much of the pupal material as is practically possible. Thereafter, the practitioner inserts into the endodontically prepared root canal a quantity of filler material, usually gutta percha. The filler material is inserted into the prepared root canal by means of a manually operated tool in which small quantities of filler material are formed on the tool, and the tool is then inserted into the root canal to, after a sequence of repeated steps, fill the canal. The same or different dental tool is then used to press and pack the filler material. After the filler material has been positioned in the root canal, the opening in the tooth is filled with a hard material in the same way that a filling in a tooth is repaired.

This typical procedure for filling root canals has disadvantages in that it is time consuming, and effectiveness of the filling procedure is not consistence or predictable. Experience has shown that it is not possible to remove all of the pulpal remanents and contaminants from a root canal with current preparation techniques. If the pulpal remanents and contaminants are thoroughly entombed in the filler material, the endodontic therapy will normally be successful. If the remanents and contaminants are not thoroughly entombed, there is a high probability of failure of the endodontic therapy. Complete entombment of the remanents and contaminants requires complete obturation of the canal system. Experience has shown that failure to completely obturate the canal system is a primary cause of failure of endodontic therapy.

For background material to improved means of filling root canals reference may be had to U.S. Pat. No. 4,894,011 entitled "Appliance For Use in Applying Filler Material To An Endodontically Prepared Root Cana" and to U.S. Pat. No. 4,758,156 entitled "Tool For Use In Applying Filler Material To An Endodontically Prepared Root Canal."

An object of the present disclosure is to provide an improved apparatus and method for filling root canals with the objective of more quickly and effectively filling canals to not only save substantial time to the endodontist or dentist, but to reduce the possibility of incomplete obturation of the canal system.

SUMMARY OF THE INVENTION

An appliance is provided for use in filling an endodontically prepared root canal. The appliance is in the form of an elongated shaft having a proximal end and a distal end. The shaft has a distal end portion formed of a diameter dimensioned to be received in a root canal. The distal end portion is spirally formed or, more broadly, has a spiral thread thereon.

Filler material, such as gutta percha, is formed on the shaft distal end portion.

The shaft includes a shank portion at the proximal end. The shank portion is configured to be received in the chuck of a dental tool having means to rotate the shaft.

The shaft distal end portion having the filler material thereon is insertable in a root canal. When so inserted, the shaft can be rotated by the dental tool to auger the filler material off of the shaft distal end portion and into the root canal. As the shaft is rotated to auger the filler material into the root canal, the shaft is slowly removed from the root canal to thereby leave the root canal completely filled with the filler material.

In one embodiment, the appliance has filler material cured thereon so as to be ready for use by an endodontist or dentist for insertion into a root canal.

In a preferred embodiment, the cured material is subject to being heated to increase the plasticity thereof before the distal end portion is inserted into the root canal.

This invention includes a method of filling an endodontically prepared root canal having the steps of:

(a) Forming an elongated shaft having a proximal end and a distal end, the shaft distal end portion being dimensioned to be received in an endodontically prepared root canal, and the shaft distal end portion being spiralled or having a spiralled thread thereon. Formed on the spiralled shaft distal end portion is a body of filler material. The shaft also has a shank portion at the proximal end.

(b) Inserting the shaft shank portion into the rotatable chuck of a dental tool.

(c) Inserting the shaft distal end portion having the filler material thereon into an endodontically prepared root canal.

(d) Activating the dental tool to rotate the shaft to auger the filler material into the root canal, the shaft being removed from the root canal as the filler material is augured therein.

In another method, the shaft is first inserted into a distal tool and then filler material is formed onto the shaft distal end portion. The distal end portion is then inserted into the root canal and the shaft rotated by the dental tool to auger the material into the root canal.

In the methods of this disclosure the filler material may be heated either after it is applied onto the shaft distal end portion or prior to applying the filler material to the shaft distal end portion. Heating the filler material, particularly when of the gutta percha type, improves the plasticity thereof to permit the filler material to more easily auger off of the shaft and more completely fill and obturate the root canal.

A better understanding of the invention will be had by reference to the following description and claims, taken in conjunction with the attached drawings.

DESCRIPTION OF THE DRAWINGS

FIG. 5 shows the end portion of a dental tool having an appliance thereon, the dental tool serving to facilitate the placement of the appliance in a root canal and for rotating the appliance while in the root canal. FIG. 5 shows the appliance without filler material thereon but showing a container of filler material in which the appliance may be inserted to receive a quantity of filler material thereon and showing diagrammatically that the filler material within the container may be heated prior to the application thereof onto the appliance.

DESCRIPTION OF THE PREFERRED EMBODIMENTS

Figure 1:
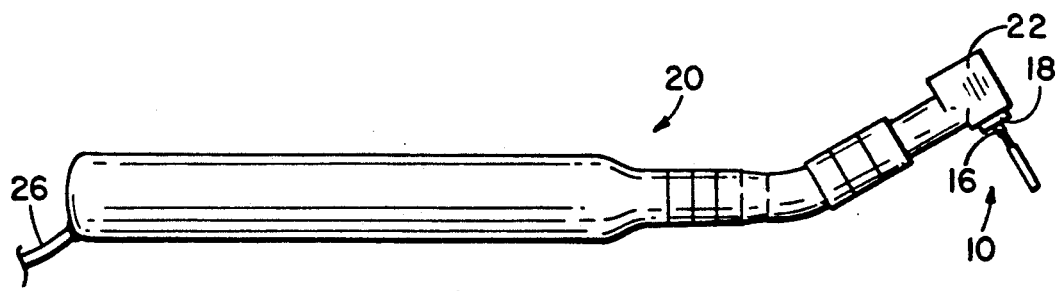
FIG. 1 is an elevational view of a typical dental tool having a chuck and having a shaft for use in filling an endodontically prepared root canal received in the chuck. The dental tool is intended to hold the shaft for insertion into a tooth and, after insertion, to rotate the shaft.
Figure 2:
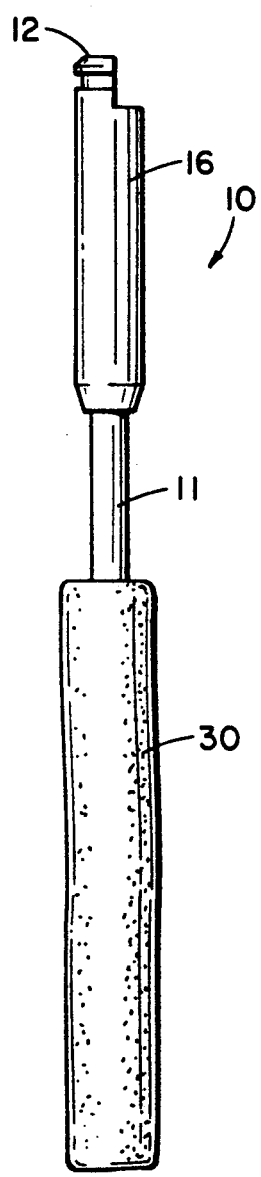
FIG. 2 is an enlarged elevational view of an appliance for use in filling an endodontically prepared root canal. The appliance in FIG. 2 is in the form of a shaft having a shank proximal end portion for receiving in the chuck of a dental tool having a reduced diameter distal end portion and having filler material received thereon.
Figure 3:
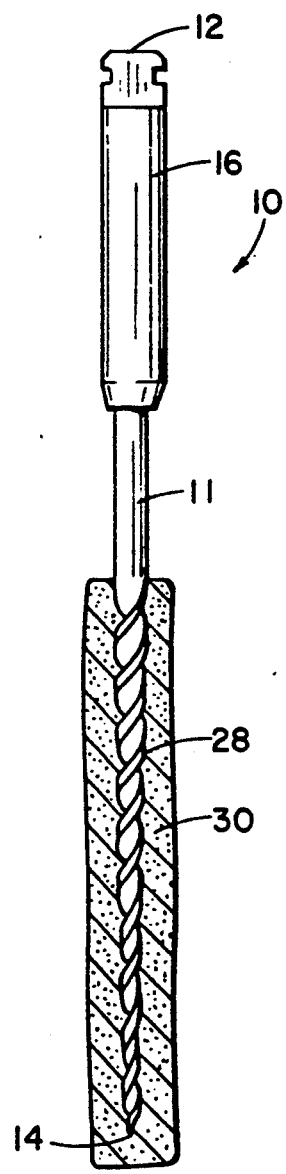
FIG. 3 is an elevational view as in FIG. 2 wherein the shank portion is rotated 90 degrees and the filler material is shown in cross-section to show the shank portion of the appliance having an auger-like configuration.

Referring to the drawings and first to FIGS. 1, 2 and 3, an appliance for use in filling an endodontically prepared root canal will be first described. FIG. 2 shows an appliance generally indicated by the numeral 10. The appliance is in the form of an elongated shaft 11 having a proximal end 12 and a distal end 14. The proximal end portion of shaft 10 is of an enlarged diameter and forms a shank portion 16 adaptable to be received in the chuck of a dental tool, generally indicated by the numeral 20.

The dental tool 20 is a representative configuration of dental tools frequently employed by dentists, such as for drilling out cavities, for rotation of cleaning brushes and so forth. The dental tool 20 has means to control the rotation of chuck 18 so that, at the will of the operator, chuck 18 can be stationary or can be rotated at a speed selected by the operator. Dental tool 20 has a head portion 22 that rotatably supports chuck 18, and a handle portion 24 that is held by the dentist or endodontist in practicing the methods of this disclosure. Attached to handle portion 20 is a conduit 26 that provides means for controlling the rotation of chuck 18. Conduit 26 may be electrical cables if the dental tool functions electrically or may be a tube if the dental tool function pneumatically.

The appliance shaft portion 11 includes a distal end portion 28 that is of reduced external diameter and dimensioned to be received into the root canal of a tooth. Typically appliances 10 are made available in a variety of sizes in which the length of distal end portion 28 may vary, and particularly wherein the diameter thereof varies.

The distal end portion 28, is shown in FIG. 3, of auger configuration, that is, the distal end portion is shaped as an auger or has an auger thread thereon. By us of the expression "auger thread" is meant a configuration of the shaft distal end portion 28 which, upon rotation of shaft 11, will cause an auger effect as hereinafter described.

Filler material 30 is formed on the shaft distal end portion 28. This filler material 30 is, by example, gutta percha. It is formed on the shaft distal end portion 28 in a quantity that is sufficient to fill a root canal with which the appliance is to be used.

The appliance 10 can be provided ready for use by a dentist or endodontist in the form in general appearance as in FIG. 2, that is, appliance 10 can be manufactured with filler material 30 applied onto shaft distal end portion 28 ready for the dentist to use to fill an endodontically prepared root canal. When supplied ready for use as shown in FIGS. 2 and 3, appliance 10 preferably has the filler material cured onto the shaft. That is, the filler material is formed onto the shaft and cured so that it remains substantially undisturbed during packaging, shipping and when handled for insertion into the chuck of a dental tool. With appliances 10 available in such a form the dentist or endodontist is saved a substantial amount of time in that as soon as the root canal is prepared and ready for filling, the dentist or endodontist merely inserts appliance 10 into a dental tool 20 and the appliance is ready for insertion into and filling a root canal.

Figure 4:
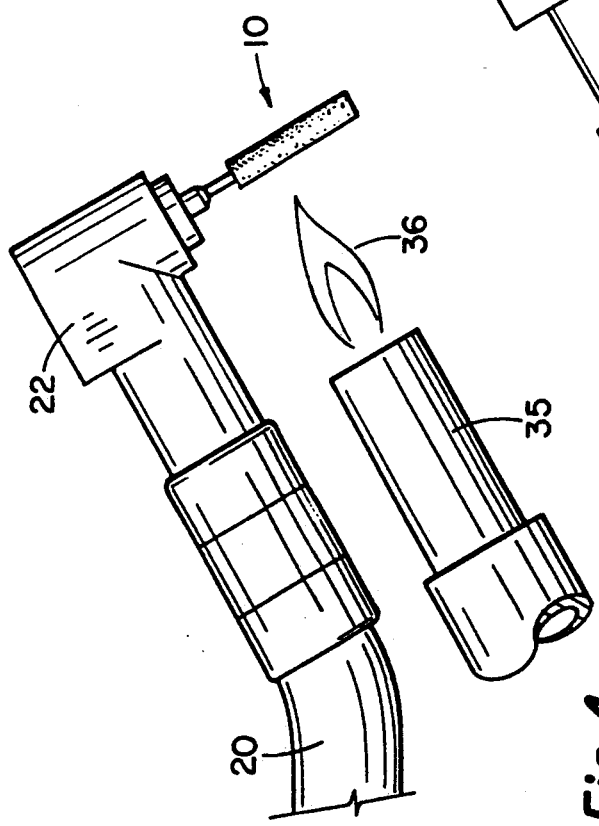
FIG. 4 is a fragmentary view of the end portion of a dental tool for use in holding and rotating an appliance showing diagrammatically a means of heating the filler material on the appliance so as to increase the plasticity thereof before the appliance having the filler material thereon is inserted into a root canal.

When the appliance of FIGS. 2 and 3 is manufactured and made available commercially to the dentist or endodontist with filler material 30 cured onto the shaft as illustrated, improved results can be obtained by heating the filler material prior to insertion into a root canal. One method of accomplishing this is illustrated in FIG. 4. The heating of filler material 30 can easily be accomplished after appliance 10 is inserted into dental tool 20 by holding the filler material over the flame of a burner, such as a typical Bunsen burner, and the appliance can be slowly rotated by the dental tool to evenly heat the filler material. When the filler material has been properly heated to increase the plasticity, the appliance may then be inserted into an endodontically prepared root canal as shown in FIG. 6.

Figure 6:
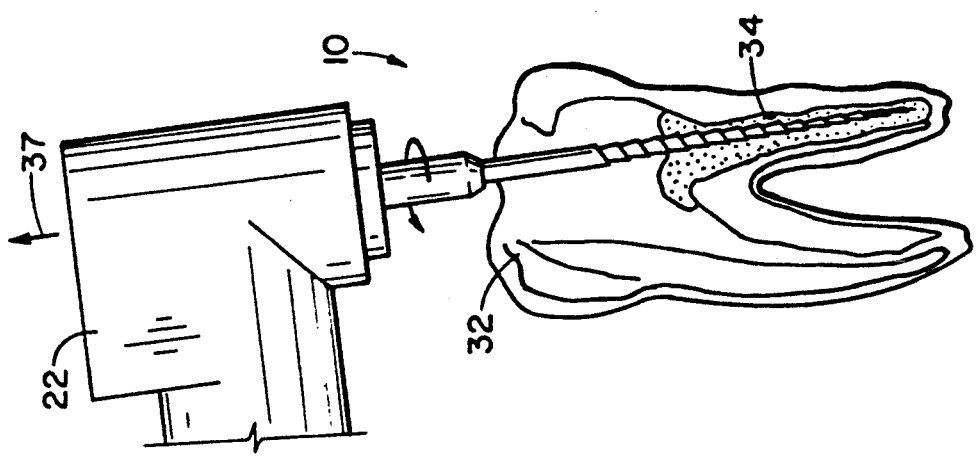
FIG. 6 is a diagrammatic view showing a tooth having an endodontically prepared root canal and showing the distal end portion of the appliance inserted into the root canal with the filler material thereon and showing means of using the appliance of FIGS. 1 and 2 for filling a root canal.

In FIG. 6 a tooth 32 has an endodontically prepared root canal 34. The dentist or endodontist has inserted the shaft portion of appliance 10 into the root canal by means of tool 20. After the appliance has been inserted the endodonists can then operate the tool to cause appliance 10 to rotate, auguring filler material 30 off of distal end portion 28 and into root canal 34. As the filler material is augured into root canal 34, shaft 11 is slowly withdrawn by moving head 22 of the tool in the direction indicated by arrow 37 to leave the root canal filled with the filler material. The auguring action of the rotating shaft serves to compact the filler material into the root canal to thoroughly fill it, force the filler material into side channels that may exist in the root canal and to thoroughly fill the canal and entomb any contaminants that may have been left in the root canal during the cleaning process.

The method of filling an endodontically prepared root canal according to the principles of this disclosure include the following steps:

(a) Forming onto an elongated shaft having a spiral thread, a body of filler material thereon.

(b) Inserting the shank shaft portion into the rotatable chuck of a dental tool.

(c) Inserting the shaft distal end portion having the filler material thereon into an endodontically prepared root canal.

(d) Activating the dental tool to rotate the shaft to auger the filler material off of the shaft and into the root canal, the shaft being removed from the root canal as the filler material is augured therein.

While practicing this method as previously indicated, it may and usually is desirable that the plasticity of the filler material be improved and this can be accomplished by heating the filler material as shown in FIG. 4 between steps (b) and (c).

Figure 5:
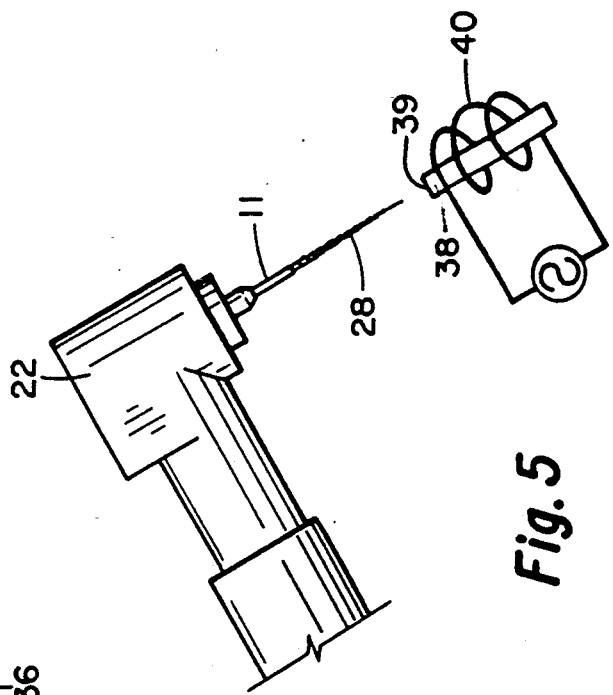
FIG. 5 is a diagrammatic view of an alternate arrangement of practicing the method of this disclosure.

Another method of using the appliance of FIGS. 2 and 3 is illustrated in FIG. 5. In this method, shaft 11 is supplied to the endodontist without having filler material already thereon. The filler material is supplied from a container, generally indicated by the numeral 38 in FIG. 5, having an open end or at least an end that can be opened. The shaft distal end portion 28 is inserted into container 38. With the shaft distal end portion inserted in the container, the filler material adheres to the shaft due to its adhesive mature. Alternately, the shaft may be rotated by tool 20 so as to auger onto itself a quantity of filler material.

The shaft is then removed from container 38 having the filler material and is ready for insertion into the root canal as shown in FIG. 6.

As has been previously indicated, it is usually desirable to heat the filler material before insertion into a root canal. In the method of FIG. 5, the filler material within container 38 can be heated so that it is ready to be used immediately after the shaft is removed from container 38. The heating of the filler material within container 38 can be such as by subjecting the container to an electromagnetic field, as indicated by coil 40. Other means of heating can include subjecting container 38 to a microwave field or to a container heated by electrical resistance or otherwise.

Container 38 may, by example, be the neck portion of a squeeze bottle or the neck portion of a syringe-type apparatus for moving filler material into the portion of the container wherein it is subject to contact by the shaft distal end portion 28.

Thus, the disclosure includes two methods of filling an endodontically prepared root canal. The first method utilizes an appliance 10 made available with filler material 30 cured thereon and ready for immediate insertion into a dental tool 20. A second method utilizes an appliance that is not supplied with filler material thereon but which is subject to forming the filler material onto the appliance for insertion into a root canal. Either method provides a superior and much more expeditious means of filling an endodontically prepared root canal as compared with the standard procedure as heretofore described, wherein the dentist manually deposits the filler material into the root canal and compacts its with a tool having no moving components.

The claims and the specification describe the invention presented and the terms that are employed in the claims draw their meaning from the use of such terms in the specification. The same terms employed in the prior art may be broader in meaning than specifically employed herein. Whenever there is a question between the broader definition of such terms used in the prior art and the more specific use of the terms herein, the more specific meaning is meant.

While the invention has been described with a certain degree of particularity, it is manifest that many changes may be made in the details of construction and the arrangement of components without departing from the spirit and scope of this disclosure. It is understood that the invention is not limited to the embodiments set forth herein for purposes of exemplification, but is to be limited only by the scope of the attached claim or claims, including the full range of equivalency to which each element thereof is entitled.

What is claimed is:

1. An appliance for use in filling an endodontically prepared root canal comprising:
   an elongated shaft having a proximal end and distal end, the shaft having a distal end portion adjacent said distal end, the distal end portion being of diameter dimensioned to be received in a root canal, the distal end portion having a spiral thread thereon;
   filler material cured onto said shaft distal end portion to a state that is, at ambient temperatures, essentially a solid, said filler material cured onto said shaft distal end portion being subject to being heated to a plastic state; and
   said shaft having a shank portion at said proximal end and said shank having means for engaging the chuck of a dental tool for rotating to said shaft, said shaft distal end portion having said filler material thereon being heatable to a plastic state and then being insertable in a root canal and adaptable to be rotated by a dental tool to auger said plastic filler material off of said shaft distal end portion and into the root canal, said shaft being removed from the root canal as said filler material is augured into the canal.

2. A method of filling an endodontically prepared root canal comprising the steps of:
   (a) forming onto an elongated shaft having a proximal end and distal end, the shaft having a distal end portion adjacent said distal end of a diameter dimensioned to be received in an endodontically prepared root canal and the shaft distal end portion having a spiral thread thereon, the shaft distal end portion having a body of filler material thereon, the shaft having a shank portion at said proximal end;
   (b) inserting the shank shaft portion into the rotatable chuck of a dental tool;
   (c) inserting said shaft distal end portion having said filler material thereon into an endodontically prepared root canal;
   (d) activating said dental tool to rotate said shaft to auger said filler material into said root canal, said shaft being removed from said root canal as said filler material is augured therein.

3. A method of filling endodontically prepared root canal according to claim 2 including, between steps (b) and (c) of:
   heating said filler material to increase the plasticity thereof.

4. A method of filling endodontically prepared root canal comprising the steps of:
   (a) inserting into the chuck of a dental tool an elongated shaft having a proximal end and distal end, the shaft having a distal end portion adjacent said distal end of a diameter dimensioned to be received in an endodontically prepared root canal, the shaft having a shank portion at said proximal end receivable in the chuck of a dental tool, and the shaft distal end portion having a spiral thread thereon;
   (b) forming filler material onto said shaft distal end portion;
   (c) inserting said shaft distal end portion having said filler material thereon into an endodontically prepared root canal;

(d) activating said dental tool to rotate said shaft to auger said filler material into said root canal, said shaft being removed from said root canal as said filler material is augured therein.

5. A method of filling an endodontically prepared root canal according to claim 4 wherein step (b) includes forming heated filler material onto said shaft distal end portion.

6. A method of filling an endodontically prepared root canal according to claim 4 wherein after step (b) and before step (c), heating said filler material formed onto said shaft distal end portion to increase the plasticity thereof.

7. A method of filling an endodontically prepared root canal comprising the steps of:

forming onto the distal end portion of an elongated shaft having a proximal end and distal end, the shaft distal end portion adjacent said distal end being of a diameter dimensioned to be received in an endodontically prepared root canal and the shaft distal end portion having a spiral thread thereon, a body of filler material, the shaft having a shank portion at said proximal end;

curing said body of filler material on said shaft distal end portion whereby said body of filler material is substantially a solid at ambient temperatures;

inserting the shaft shank portion into the rotatable chuck of a dental tool;

heating said filler material that is cured onto said shaft before or after insertion into a dental tool chuck to change the state thereof from substantially a solid to a plastic state;

inserting said shaft distal end portion having said heated filler material thereon into an endodontically prepared root canal; and activating said dental tool to rotate said shaft to auger said heated filer material into said root canal, said shaft being removed from said root canal as said filler material is augured therein.

* * * * *